(12) United States Patent
Pressacco et al.

(10) Patent No.: US 12,121,451 B2
(45) Date of Patent: Oct. 22, 2024

(54) SHOULDER PROSTHESIS (71) Applicant: Limacorporate S.p.A., San Daniele del Friuli (IT)

(72) Inventors: Michele Pressacco, Martignacco (IT); Andrea Fattori, Cividale del Friuli (IT); Thomas Ferro, Bicinicco (IT); Nicola Del Negro, San Daniele del Friuli (IT)

(73) Assignee: Limacorporate S.p.A., San Daniele del Friuli (IT)

( * ) Notice: Subject to any disclaimer, the term of this patent is extended or adjusted under 35 U.S.C. 154(b) by 0 days.

(21) Appl. No.: 17/921,183

(22) PCT Filed: Mar. 3, 2022

(86) PCT No.: PCT/EP2022/055419
§ 371 (c)(1),
(2) Date: Oct. 25, 2022

(87) PCT Pub. No.: WO2022/189257
PCT Pub. Date: Sep. 15, 2022

(65) Prior Publication Data
US 2023/0404766 A1 Dec. 21, 2023

(30) Foreign Application Priority Data

Mar. 12, 2021 (IT) .......................... 102021000005870

(51) Int. Cl.
*A61F 2/40* (2006.01)
*A61F 2/30* (2006.01)

(52) U.S. Cl.
CPC ........ *A61F 2/4081* (2013.01); *A61F 2/30749* (2013.01); *A61F 2002/30245* (2013.01);
(Continued)

(58) Field of Classification Search
CPC ........ A61F 2/40; A61F 2/4081; A61F 2/4014; A61F 2/4003; A61F 2/30749
See application file for complete search history.

(56) References Cited

U.S. PATENT DOCUMENTS 6,595,993 B2 * 7/2003 Donno ............... A61B 17/8042
606/295
9,844,440 B2 * 12/2017 Kovacs ............... A61F 2/30734
(Continued)

FOREIGN PATENT DOCUMENTS

EP  1 488 764 A1  12/2004
EP  2 787 932 A1  10/2014
(Continued)

OTHER PUBLICATIONS

International Search Report dated May 19, 2022 issued in connection with PCT/EP2022/055419.
Written Opinion of the International Searching Authority dated May 19, 2022 issued in connection with PCT/EP2022/055419.

*Primary Examiner* — Brian A Dukert
(74) *Attorney, Agent, or Firm* — Akerman LLP (57) ABSTRACT The present invention relates to a shoulder prosthesis comprising:—a metaglene element (2) or baseplate;—a pin (3) projecting from said metaglene element (2);—a through-hole (11) in the centre of said metaglene element (2);—at least one through-hole (5) formed in a periphery of the metaglene element (2) with respect to said central through-hole (11);—a glenosphere element (12) opposite said pin (3) with respect to said metaglene element (2);—a central compression screw (9) housed in said through-hole (11) in the centre of said metaglene element (2) and having a head abutting onto the bottom of said hole (11); and—wherein the central through-hole (11) has an opening (11A) that is threaded in a stretch to receive the end of a safety screw (18) passing through the glenosphere element (12);—a connector element (13) between the metaglene element (2) and the
(Continued)

glenosphere element (12), the metaglene element (2) providing a seat (14) for housing the connector element (13) projecting around the central through-hole (11).

14 Claims, 9 Drawing Sheets

(52) U.S. Cl.
CPC ............... *A61F 2002/30332* (2013.01); *A61F 2002/30433* (2013.01); *A61F 2002/30476* (2013.01); *A61F 2002/30774* (2013.01); *A61F 2002/30784* (2013.01); *A61F 2002/4085* (2013.01)

(56) References Cited

U.S. PATENT DOCUMENTS

| | | | |
|---|---|---|---|
| 10,736,751 B2* | 8/2020 | Hodorek | A61F 2/30749 |
| 2018/0064537 A1* | 3/2018 | Pressacco | A61F 2/30749 |
| 2020/0030108 A1* | 1/2020 | Orphanos | A61F 2/4014 |

FOREIGN PATENT DOCUMENTS

| | | |
|---|---|---|
| WO | 01/47442 A1 | 7/2001 |
| WO | 2011/098890 A1 | 8/2011 |
| WO | 2015/103090 A1 | 7/2015 |

* cited by examiner

SHOULDER PROSTHESIS

CROSS-REFERENCE TO RELATED APPLICATIONS

This application is a national phase of PCT/EP2022/055419, filed Mar. 3, 2022, and claims priority to Italian Patent Application No. 102021000005870, filed Mar. 12, 2021, the entire contents of both of which are hereby incorporated by reference.

FIELD OF APPLICATION

The present invention relates to a shoulder prosthesis for the joint of a humeral head with respect to the relative scapula.

In general the present invention finds application in the orthopaedic prosthesis field for shoulder surgery.

PRIOR ART

The anatomical shoulder joint, or scapula-humeral joint, essentially comprises the humeral head, that is shaped as a sphere portion, and the glenoid cavity, or glenoid, of the scapula, that has a slightly oval shape and is not very deep.

For the correct shoulder functioning a key role is played by the four muscles and tendons of the rotator glenosphere, that keep the humeral head firmly approached and centred on the glenoid and provide the internal and external rotation force, as well as by the deltoid that is a strong muscle that is crucial for the arm raising movements.

There are various situations in which a shoulder prosthesis intervention may be necessary.

The most frequent one is arthrosis, that involves, compared to a normal shoulder, the loss of the coating cartilage with subsequent disappearance of the joint space between humerus and scapula, the subsequent deformation of the joint surfaces and the formation of bone spurs called osteophytes.

Sometimes this spontaneously occurs with aging, other times this is favoured and conditioned by previous damages to the joint, for example serious traumas or repeated shoulder dislocations.

There are then other situations such as the occurrence of rheumatic diseases like rheumatoid arthritis, psoriatic arthritis and the like or the outcomes of poorly healed fractures There is a right indication to resort to a prosthesis implantation when one of the above-listed diseases leads to a severe and scarcely controllable pain and to a considerable loss of shoulder movements, whereby the patient is no more able to perform its daily activities.

There are numerous currently available solutions.

In particular, the so-called "total" prosthesis are available, with the replacement of both joint sides, both the humeral head and the scapular glenoid, or the prostheses concerning only the humeral side, in that case it is technically called "hemiarthroplasty".

A "total" prosthesis must be adopted when both the humeral component and the glenoid one are degenerated or impaired.

According to an "anatomical" model a component with a convex humeral head is coupled to a scapular component with a concave surface or cup, that can be composed of a base called metaglene, coupled with an insert, and, as its name suggests, the structure of this component recalls the shape of the glenoid cavity.

Another "total" prosthesis model that has become successful in more recent years is the so-called "reverse prosthesis", composed of the metal base that comprises a glenosphere, and it is characterised by a structure being substantially the opposite of the anatomical structure of the shoulder: a hemispherical convex component is fixed to the scapula, while the concave surface for housing the hemispherical part is on the humerus side.

The "anatomical" model is preferred in the absence of rotator cuff damages, allowing therefore that the anatomical biomechanics and the joint stability are still ensured.

The "reverse" model is instead preferred in case of rotator cuff impairment due to an irreparable injury, involving that the anatomical biomechanics and the joint stability are impaired to the extent that a traditional anatomical prosthesis is not able to lead to an improvement of the patient's clinical status.

Even the prosthesis materials have undergone a strong innovation in recent years, with the development of coatings that are more biocompatible and respectful of the host tissue, being it both bone and cartilage.

In this regard, specific solutions are also known, described for example in the European patent application No. EP1488764A1 of the same Applicant and in the International application No. WO01/47442A1 of DEPUY.

Despite the presence of the above solutions and of the above updates according to the prior art, the need is still felt to improve the features thereof in order to have a better clinical result.

More particularly, it is well known that assembling the glenosphere to the glenoid component is difficult due to the extremely reduced available spaces. This determines an obstacle to the accuracy of its positioning with a subsequent loss of time as well as with the risk of an incorrect assembling of the cones and the subsequent implantation failure.

The technical problem underlying the present invention is to provide a shoulder joint prosthesis in which the implantation of a reverse prosthesis allows an easy and accurate assembling of the spherical body in the glenoid cavity, facilitating the surgeon's work.

Another object of the invention is to devise a prosthesis that is able to improve the fixation between the prosthesis and the bone, with a subsequent improvement in bone growth.

A further object of the invention is also to provide a solution with reduced dimensions, in order to reduce the invasiveness of the prosthesis both for the implantation step and for the following rehabilitation step. In other words, limited dimensions are to be kept both longitudinally and transversely.

Still another object of the present invention is to take into consideration the natural anatomical differences existing between the several patients and thus to provide a certain number of options to the surgeon in order to ensure the best biomechanical solution.

Finally, the object of the invention is to provide a solution that is suitable both an "anatomical" prosthesis model and for a "reverse" prosthesis model.

SUMMARY OF THE INVENTION

The solution idea underlying the present invention is to provide a particularly compact solution that exploits a compression action both between the components of the prosthesis to be assembled together and with respect to the anatomical seat in which the latter is housed.

The above technical problem is solved by a shoulder prosthesis comprising:
- a metaglene element or baseplate;
- a pin projecting from said metaglene element;
- a through-hole in the centre of said metaglene element;
- at least one through-hole formed in a periphery of the metaglene element with respect to said central through-hole;
- a glenosphere element opposite said pin with respect to said metaglene element;

characterized in that it further comprises:
- a central compression screw housed in said through-hole in the centre of said metaglene element and having a head abutting onto the bottom of said hole;
- said central through-hole having an opening that is threaded in a stretch to receive the end of a safety screw passing through the glenosphere element;
- a connector element (13) between the metaglene element (2) and the glenosphere element (12), said metaglene element (2) providing a seat (14) for housing said connector element (13) projecting around said central through-hole (11).

Advantageously, the present solution, by means of the central compression screw, that can be adjusted to different lengths according to need, allows a greater compression and thus a primary stability of the implant.

Preferably, the connector element between the metaglene element and the glenosphere element is also incorporated between said elements.

Moreover, preferably, the seat for housing said connector element is formed as a single piece projecting around said central through-hole.

Moreover, the connector element comprises a cone portion and said connecting seat is shaped with some crenelated portions angularly spaced apart from each other and crown-projecting from the surface of the baseplate facing the side of the glenosphere.

A portion of said connector element has a positive engagement with said glenosphere element that is consolidated by the insertion of said safety screw.

Moreover, the connector element can be coupled to said glenosphere element by means of a connecting portion with an axial dimension adapted to generate an offset of the rotation centre of the glenosphere (12) comprised between 1 mm and 10 mm.

According to a preferred embodiment the pin is removable and constrained to a projection of the baseplate. Alternatively, the baseplate and the pin are made as a single piece but the central through-hole passes completely through them.

Multiple through-holes are also provided, having respective axes (A-A) that are slanted with respect to a central axis (X-X) of said metaglene element and arranged perimetrically to the central through-hole, to house perimetrical fixing screws.

It should also be noted that a locking element forming a closure after the insertion of the fixing screw is associated at the opening of said through-hole formed peripherally for the perimetrical fixing screw. This fixing screw is preferably, as in the represented embodiment, a spherical head.

The locking element is a disc perimetrically equipped with at least one thread turn and it provides a hemispherical protuberance; the head of said fixing screw provides instead a frustoconical seat for housing said hemispherical protuberance. In the represented embodiment, locking is thereby ensured by the fact that the axis of the truncated cone of the fixing screw head always passes through the centre of the locking element and by the fact that it coincides with the centre of the spherical head of the fixing screw.

The baseplate of the present solution has smaller dimensions with respect to known solutions, for example it has an essentially cylindrical body and a diameter that is less or equal to 25 mm.

Obviously, nothing prevents the same solution described here from being applied to baseplates having a greater diameter.

Moreover, the baseplate comprises a trabecular structure or a surface coating layer on a surface configured to be in contact with a bone.

The prosthesis of the present solution can be configured to be convertible, with the central hole further adapted to house a liner insert according to an anatomical configuration.

In this anatomical configuration, the liner insert is thus assembled opposite the pin of the baseplate in place of the glenosphere element and connector element.

Further features and advantages will become apparent from the following detailed description of a preferred but not exclusive embodiment of the shoulder prosthesis according to the present invention, referring to the attached figures given by way of non-limiting example.

DETAILED DESCRIPTION

With reference to the attached figures, a first embodiment of a shoulder prosthesis is globally and schematically indicated with 1, made in accordance with the present invention, defined hereafter for brevity with prosthesis 1, and prosthesis 1' in an alternative embodiment thereof.

Specifically a so-called reverse prosthesis is represented here, but the present invention finds application also in the so-called anatomical prostheses, as it will become apparent hereafter.

In particular, the prosthesis 1 or 1' comprises an intermediate metaglene element 2. This element 2 can represent by itself a so-called prosthesis baseplate, or it can cooperate with a pin 3 or peg of bone implantation in the glenoid cavity.

As will be seen in greater detail hereafter, in order to have a prosthesis system that is suitable also in case of bone deficit, the baseplate 2 is also made in a so-called augmented version, that is available in a range of different configurations; it is thereby possible to recover different types of bone deficit of the glenoid, restoring an optimum condition both in terms of bone reconstruction and in terms of tissue tensioning.

The pin 3 actually projecting from the metaglene element 2 is associated at a base of the metaglene element 2 to be turned towards the glenoid cavity.

Figure 3:
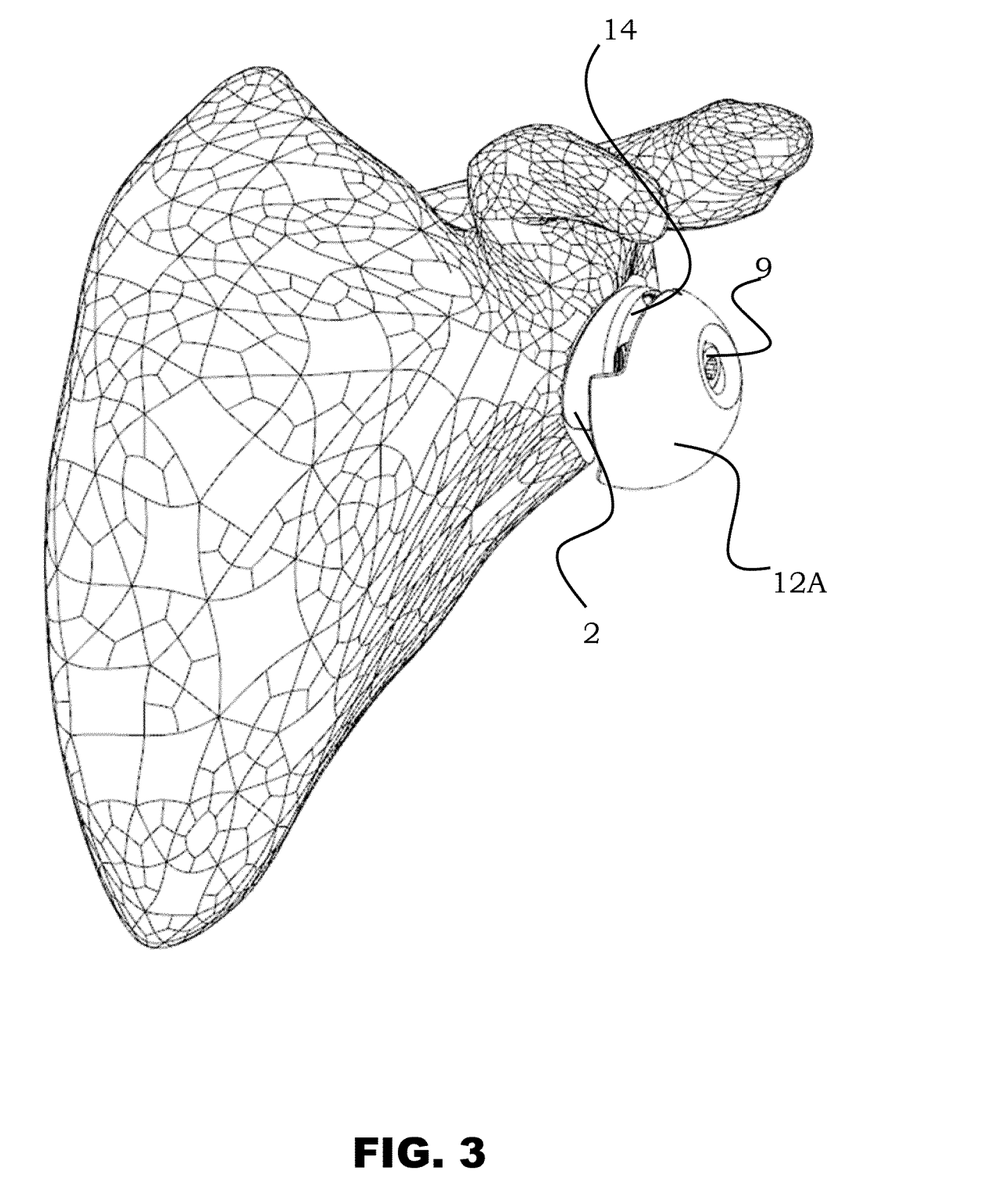
FIGS. 3 and 4 show a shoulder prosthesis according to the invention in a combined seat obtained in a glenoid.
Figure 4:
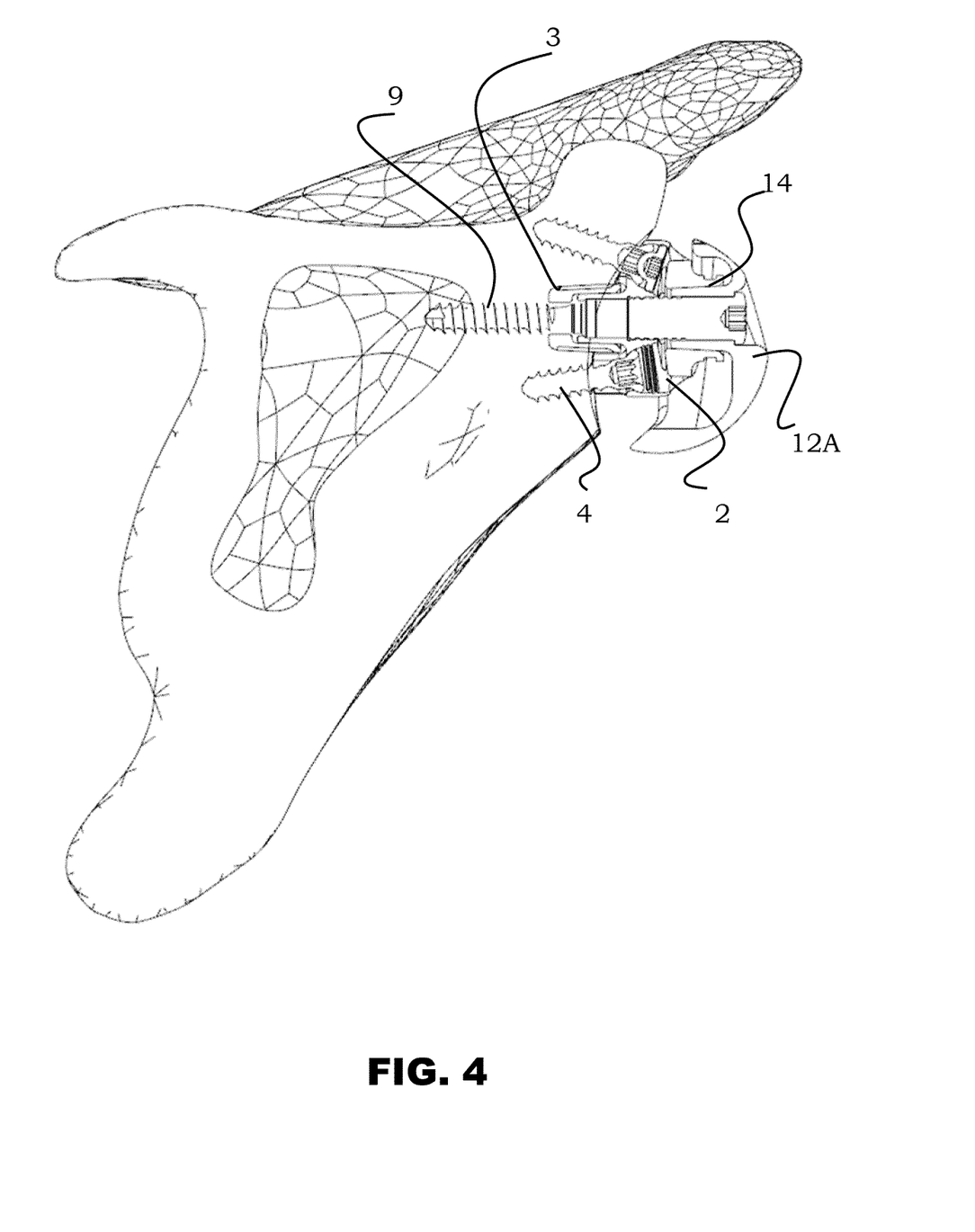

The metaglene element 2 is a substantially cylinder-shaped element that is positioned together with the relative pin 3 on the glenoid or humerus, depending on whether it is an anatomical or reverse prosthesis. In general, the pin 3 is implanted by forcing it by interference, screwing it, or cementing it, in a combined seat obtained in the glenoid, as can be seen in FIGS. 3 and 4.

Figure 1:
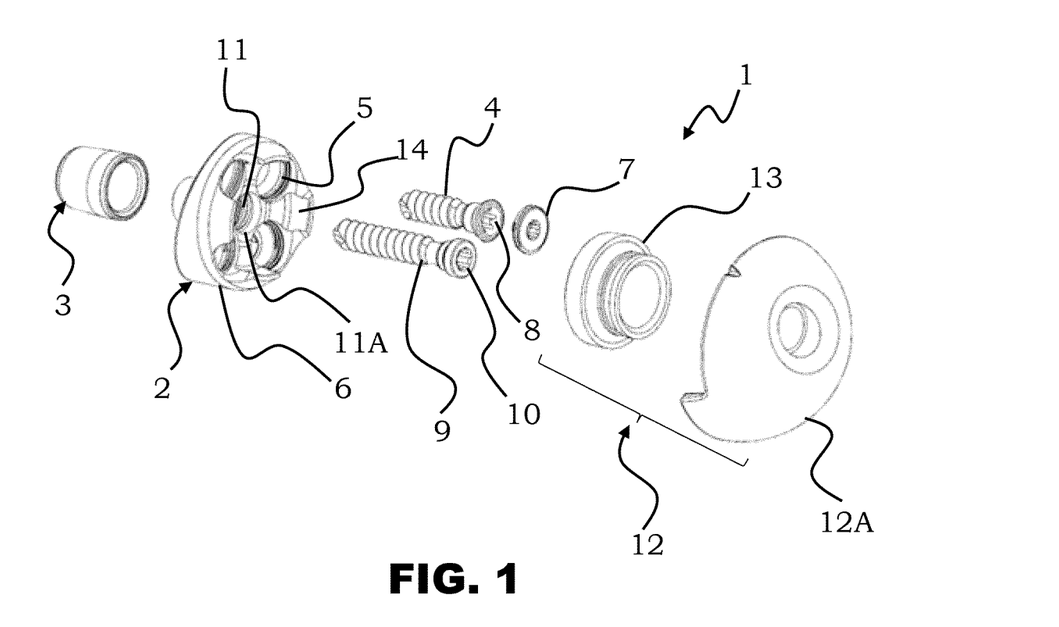
FIG. 1 shows an exploded view of a shoulder prosthesis according to a first embodiment according to the invention.
Figure 2A:
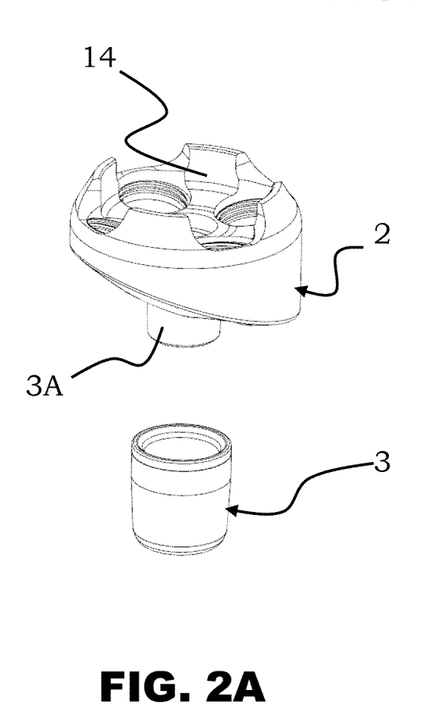
FIGS. 2A and 2B show two embodiments of a detail of the shoulder prosthesis of FIG. 1.
Figure 2B:
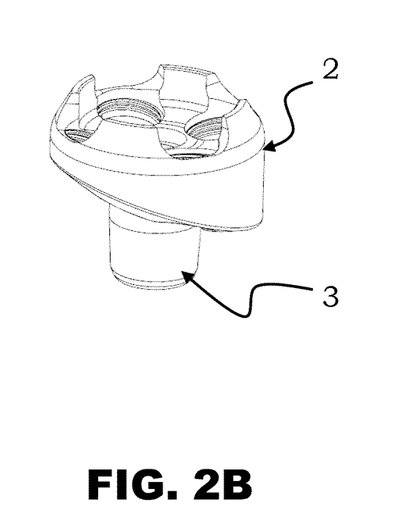

As can be seen in FIGS. 2A and 2B, the metaglene element 2 and the pin 3 can be removable and detachably associated (FIG. 2A) or they can constitute a single monolithic element formed as a single piece (FIG. 2B). In the first case the metaglene element 2 is provided with a projection 3A on which the pin 3 is fixed; while, in the second case there is obviously no need for an association step between the two components, on the contrary the pin 3 represents the projection itself of the element 2.

In the embodiment represented in FIG. 2A the coupling is obtained by conical coupling, preferably of the Morse cone type, but nothing prevents a different type of coupling from being adopted. In case of modularity between the element 2 and pin 3 all the baseplates 2 (also those otherwise augmented) can be coupled with all the pins 3 (of different lengths).

Advantageously, with respect to a pin 3 currently used in a SMR MB TT prosthesis system (acronym for Shoulder Modular Replacement Metal Back Trabecular Titanium), the dimensions of the pin 3 of the present description are significantly reduced due to the adoption of the connector element 13 with the housing seat 14 thereof that allows the number of the required fixing components to be reduced (merely by way of example: from a diameter of Ø 10.37 mm in a modular version and of 9.3 mm in a single-piece version with respect to a diameter of Ø 11.37 mm.

On the contrary, in case the two components 2 and 3 are detachable from each other, different metaglene elements 2 can be associated with pins 3 having a different length, therefore reducing the number of different elements to be produced.

Furthermore, the metaglene element 2 can provide a surface coating 22, in particular at the surface contacting the bone. This surface coating 22 can be, for example, made of trabecular titanium.

A through-hole 11 that is located centrally and actually coaxial along a main axis X-X with the projection portion 3A of the metaglene 2, or anyway with the pin 3, is provided in the body of the metaglene 2

A central compression screw 9 is housed in the hole 11 and it passes through the metaglene element 2 and the pin 3 projecting from these elements 2, 3 until it is implanted by screwing in the glenoid. The central compression screw 9 has a head 10 with an Allen wrench seat, or similar shaped recessed seat, to be screwed by means of a special and combined wrench.

Figure 5:
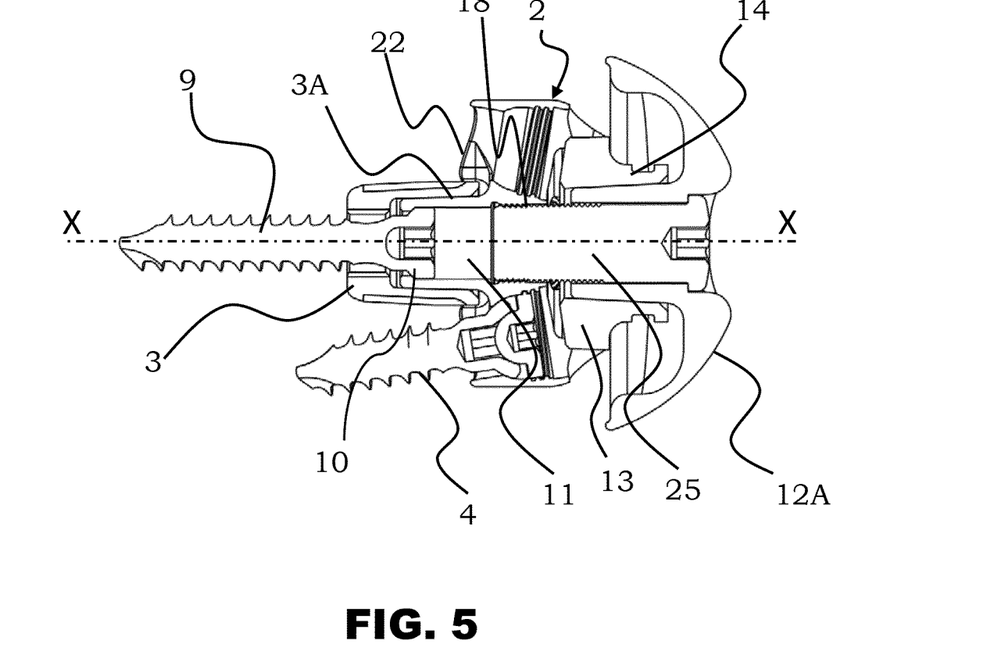
FIG. 5 shows a sectional view of FIG. 1.
Figure 6:
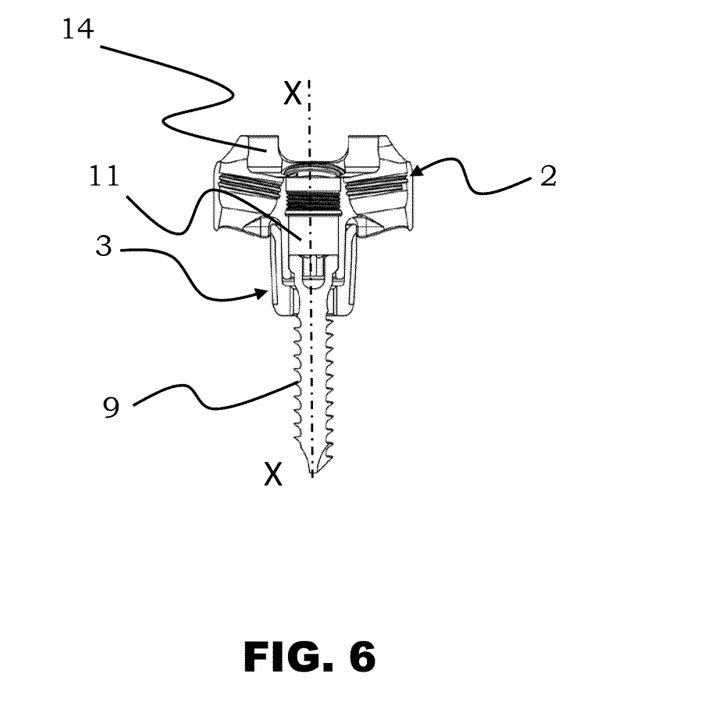
FIG. 6 shows another sectional view of FIG. 1.

The head 10 of the screw 9 abuts onto the bottom of the hole 11, as shown in the section of FIG. 5. The bottom of the hole 11 has a slightly narrowed diameter with respect to the diameter of the hole 11 itself.

The opening 11A of the central hole 11 is threaded in at least one stretch 18 to house the threaded end 24 of a further safety screw 25 that will be discussed hereafter.

The central compression screw 9 can have, as appropriate, different lengths. The central compression screw 9 allows an optimum osteointegration being able to consolidate the implantation of the pin 3 in the glenoid cavity.

Moreover, in case the metaglene element 2 and the pin 3 are detachable from each other, this screw 9 cooperates with these elements 2, 3 in preventing an undesired disconnection thereof. Moreover, it generates a beneficial compression between the overall prosthesis implant and the bone.

Some seats 5 for housing peripheral/lateral fixing screws 4 are provided around the central through-hole 11.

In essence, the metaglene element 2 and the relative pin 3 are stabilized in situ, increasing the implant holding degree, with the aid of at least one peripheral fixing screw 4 inserted in a corresponding through-hole seat 5 provided in the body of the metaglene 2. In a preferred embodiment the screw 4 has a sphere-shaped head that allows it to be conveniently oriented in different directions.

Multiple through-hole seats 5 for pinpherical/lateral fixing screws 4 are provided.

The through-hole seats 5 are provided in the number of four but they can be also less or more in number, consistently with the possibility of forming them around the central hole 11.

Each seat 5 has a countersunk and threaded insertion portion to house by screwing the corresponding spherical shape of the head of the fixing screw 4.

In the present embodiment illustrated in the attached Figures four fixing screws 4 essentially arranged like a cross around the central through-hole 11 are provided.

The fixing screws 4 can have a stem, as appropriate, with a different length and diameter.

As can be seen in the Figures these fixing screws 4 are extended along axes diverging from each other when implanted. More particularly, as shown in the example of FIG. 7, each screw 4 is extended along an axis A-A that is slanted with respect to the main axis X-X of the metaglene element 2 and with an angle of inclination that generally varies by an amplitude a depending on the recessed conformation of the respective housing seats 5, as well as on the size of the fixing screws 4 themselves.

The axis A-A is actually the axis of the holes 5 that is slanted with respect to the central axis X-X of the metaglene element (2).

Figure 7:
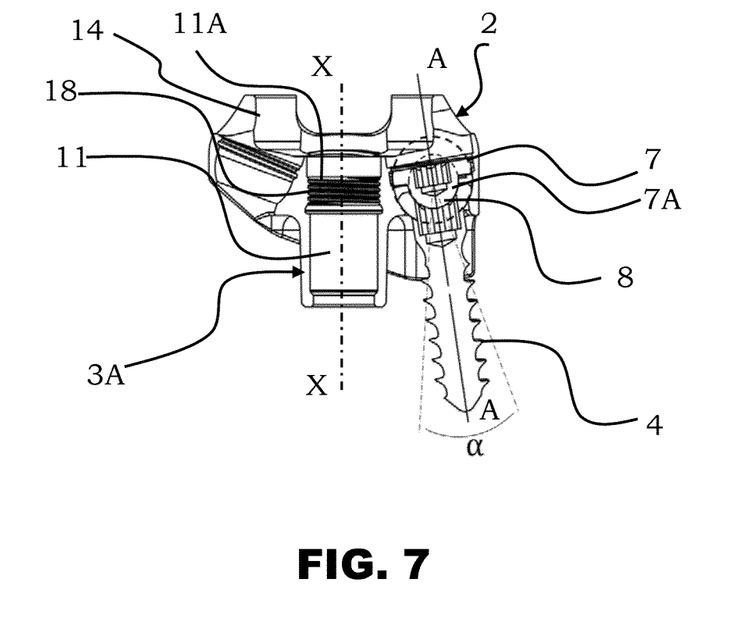
FIG. 7 shows a detail of FIG. 4.
Figure 8:
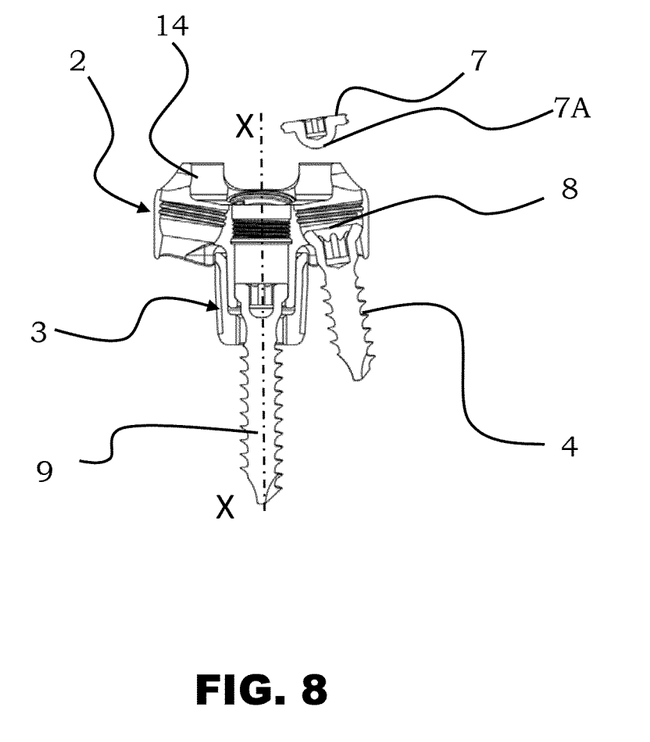
FIG. 8 shows another sectional view of FIG. 1 with a locking element.

The prosthesis component that is equipped with at least one of the fixing screws 4 is represented in particular in FIGS. 7 and 8.

When simply inserted according to the corresponding pilot hole angle, the screws 4 act by compression but without being it possible to prevent a rotation due to the load of each fixing screw 4 around its own hole 5, obviously provided that this rotation is within the range admitted by the conformation of the metaglene element 2.

Figure 9:
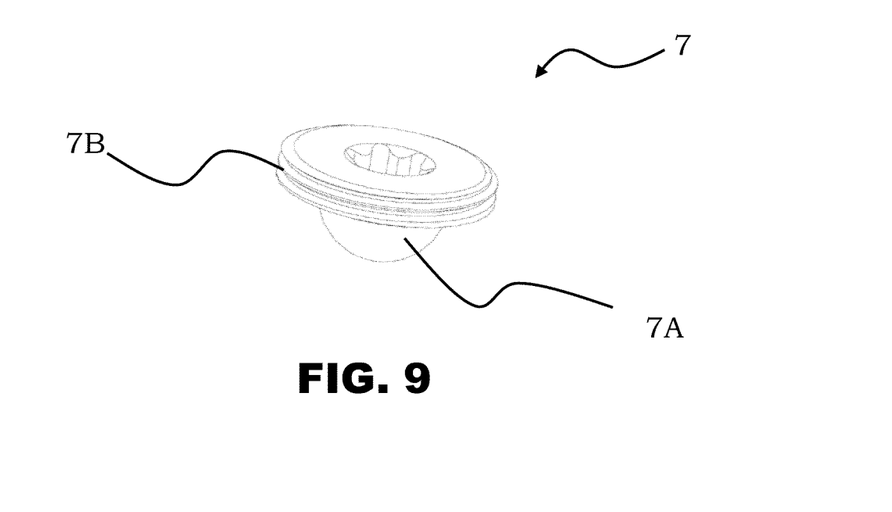
FIG. 9 shows a perspective view of the locking element of FIG. 6.

The present invention also provides a device for preventing the rotation of the screws 4 around their own axis after implantation. As can be seen in FIG. 8, a removable locking element 7 has been devised, that in a preferred embodiment is schematically represented in FIG. 9. Furthermore, the locking element 7 allows the screws 4 to be inserted with different angles according to a range of angles comprised within an opening cone α, as can be seen in FIG. 7.

The locking element 7 is actually a locking cap that is similar to the head alone of a screw with at least one perimetrical thread turn 7B. This element 7 has an Allen wrench seat and an opposite hemispherical protuberance 7A.

Each screw 4 has a frustoconical seat 8 in which the hemispherical protuberance 7A of the locking element 7 is housed.

In essence, the locking element 7 is screwed into the internal thread of a hole 5 after the corresponding fixing screw 4 has already been inserted and screwed, one or more turns of the locking element 7 allows it to be fixed as a cap onto the opening of the hole 5, the protuberance 7A being housed in the frustoconical seat in the head of the screw 4. However, nothing prevents a locking element 7 that can be inserted on the opening of the hole 5 only by pressure from being otherwise provided.

With the presence of the locking element 7 the possible release in rotation of the screws 4 is prevented due to the friction generated by the contact pressure between the hemispherical surface 7A of the locking element 7 and the frustoconical surface of the seat that is present in the head of the screw 4.

The fact of having an identical conformation of the head of the screws 4 regardless of the stem allows a standardised conformation for the locking elements 7 to be created.

The structure of the shoulder prosthesis 1 also comprises a glenosphere element 12 to be assembled on the metaglene element 2 in a position opposite the pin 3.

Figures 14B, 14C:
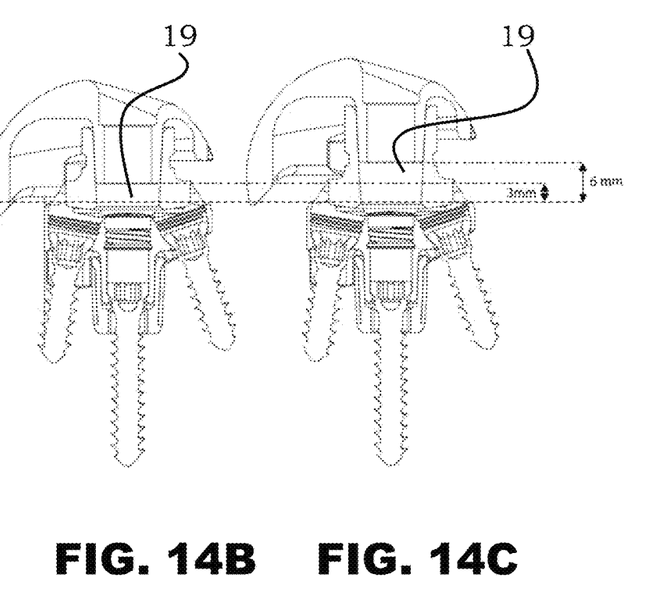
Figure 15:
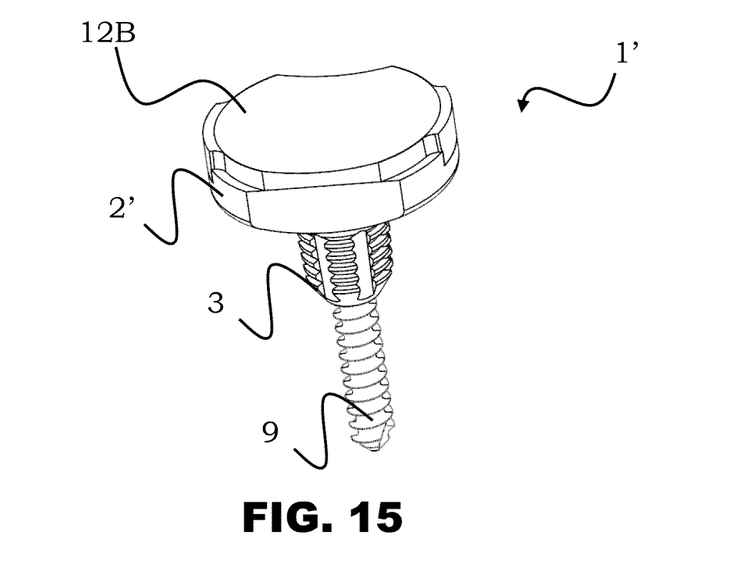
FIG. 15 shows a perspective view of a reverse prosthesis according to the invention.
Figure 16A:
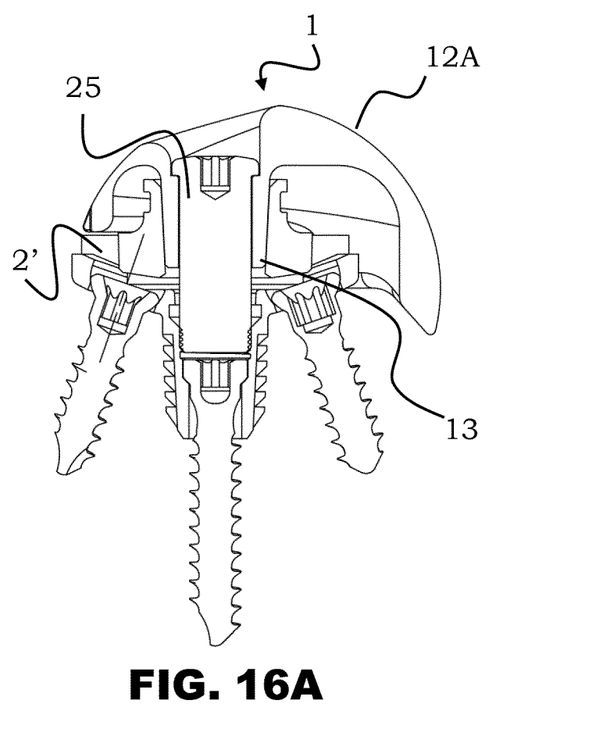
FIGS. 16A and 16B show two revision steps of a shoulder prosthesis according to the invention between a reverse configuration and an anatomical configuration.
Figure 16B:
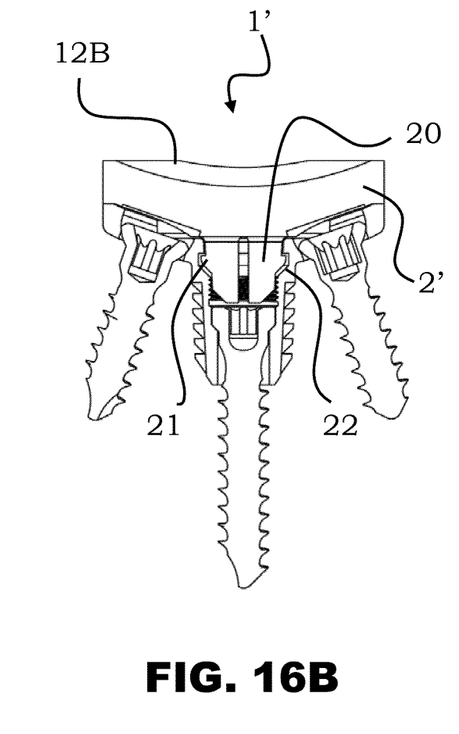

In the embodiment represented in FIGS. 1 to 14C and 16A a prosthesis 1 of the reverse type is illustrated, while FIGS. 15 and 16B concern an anatomical prosthesis.

In case of reverse prosthesis, the glenosphere element 12 comprises a substantially hemispherical element 12A, called glenosphere 12A, and a connector element 13 with an annular body through which the glenosphere 12A is coupled to the metaglene element 2.

Advantageously, the connector element 13 comprises two portions 15, 19 and is incorporated between the glenosphere and the baseplate.

Figure 10:
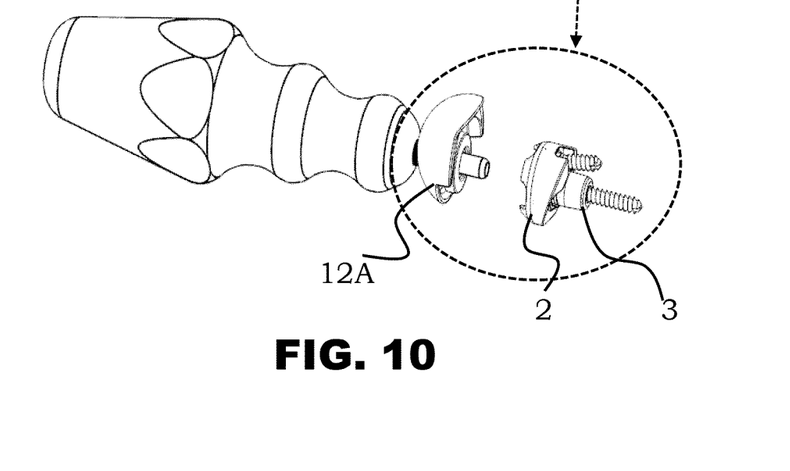
FIG. 10 shows an embodiment of a coupling mode of a substantially hemispherical element of the shoulder prosthesis according to the invention.
Figure 10D:
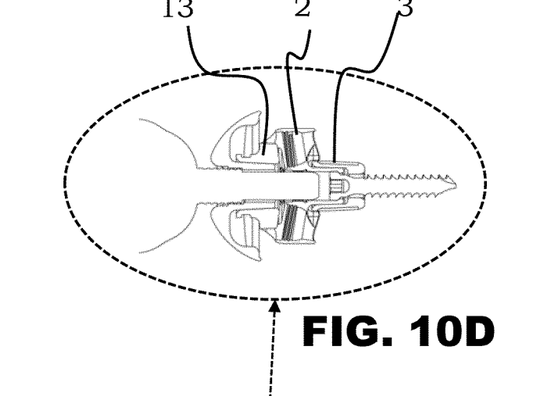
FIG. 10D shows a detail of FIG. 8.

The glenosphere 12A and the connector element 13 are preferably coupled, as shown in FIG. 10, and in detail in FIG. 10D, or also in FIG. 13, first by positive engagement, being it preferably conical, even more preferably with a male cone at the glenosphere 12A and a female cone at the connector element 13, but the other way around is also possible, and then by screw coupling, which will be discussed hereafter.

Such an embodiment allows an easy coupling of the whole prosthesis structure.

The coupling between the connector element 13 and the metaglene element 2 or baseplate is instead performed between a connecting seat 14 of the metaglene element 2 adapted to house a portion 15 of the connector element 13 and formed around the central hole 11 of the baseplate 2. This seat 14 is substantially formed projecting towards the glenosphere element (12) and is defined and delimited by some crenelated portions 28 angularly spaced apart from each other and crown-projecting from the surface of the baseplate facing the side of the glenosphere 12A.

Figure 11:
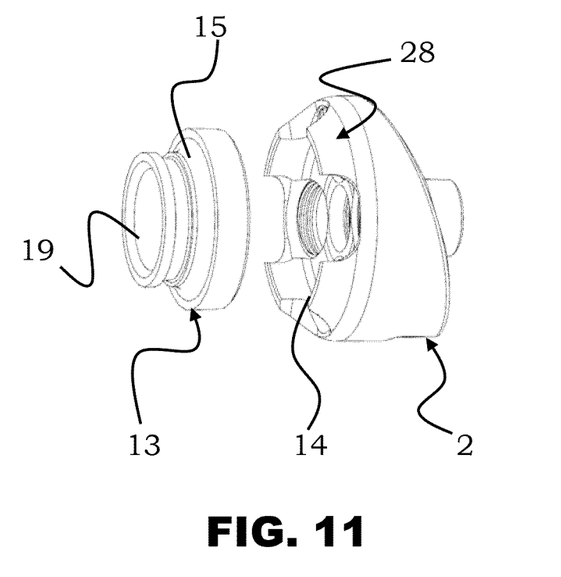
FIG. 11 shows a particular view of a first embodiment of a coupling mode between a connector element and a metaglene element in the shoulder prosthesis according to the invention.

More specifically, according to a first embodiment that is visible in FIG. 11, the connector element 13 comprises an annular edge portion 19 that is coaxial with a cone portion 15.

The connecting seat 14 of the baseplate has the shape of a cone-tapered recess, with the portion 15 configured for a conical coupling between the male cone on the connector element 13 and the female cone 14 of the baseplate 2.

This coupling has been defined with particular accuracy since the distinct crenelated portions 28 that form in a crown shape the female seat 14 are obtained by a single turning step and later truncated and they millimetrically couple with the portion 15 of the connector 13.

The cone portion 15 is fully incorporated in the seat 14 while the annular edge portion 19 houses a conical part of the glenosphere until it is in turn fully incorporated by the glenosphere element 12.

The connector 13 is hence nested between the two metaglene 2 and glenosphere 12 elements.

Since the whole coupling between the seat 14 of the metaglene element 2 and the portion 15 of the connector element 13 is thus within the dimensions of the metaglene element 2, possible interferences with the surrounding soft tissues can be avoided.

According to an alternative embodiment, different portions for positive engagement between the metaglene element 2 and the connector element 13 can be provided.

Figure 12A:
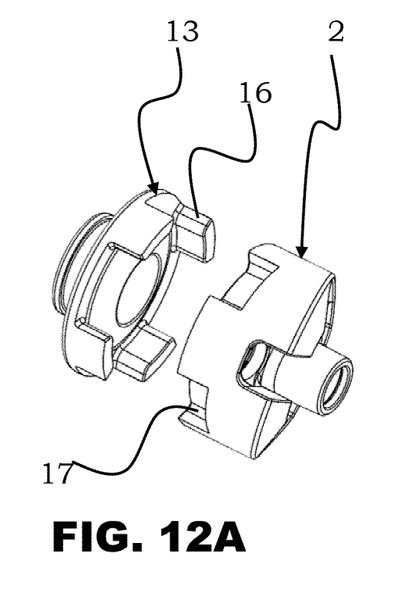
FIGS. 12A and 12B show two perspective views of a second embodiment of a coupling mode between a connector element and a metaglene element in the shoulder prosthesis according to the invention.
Figure 12B:
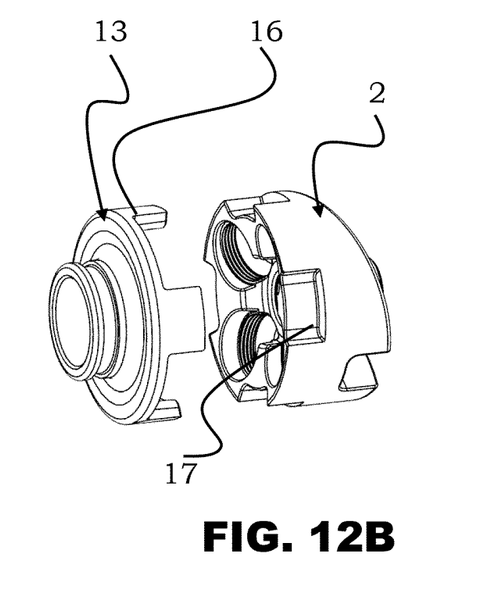

More particularly, in an exemplary embodiment illustrated in the two views of FIGS. 12A and 12B, some tabs 16 angularly spaced apart and projecting from the connector element 13 can be provided, intended to engage in corresponding slots 17 provided at the external perimetrical surface 6 of the baseplate element 2. In the example that is illustrated here for merely indicative purposes these tabs 16 are four in number.

This solution is obviously alternative to the previous one, since it is necessary to insert "in phase" the four tabs 16 of the connector element 13 with the four slots 17 of the metaglene element 2, and it is thus more difficult to assemble during the surgical operation with respect to the previous one, requiring then however the introduction of the screw.

Nothing clearly prevents a different number of tabs 16 and slots 17 from being adopted or a different type of positive engagement from being provided.

The first embodiment, represented by way of example in FIG. 11 allows to "orient" the construction formed by the glenosphere 12A and the connector 13 during the insertion step and, once the optimal position for the surgeon has been found, to impact everything. This is often necessary because not all the glenospheres are symmetrical, but some have asymmetries that determine optimal implantation positions.

For this requirement, the first embodiment that has no obligatory insertion directions is thus preferable.

Vice versa, in the alternative embodiment of FIGS. 12A and 12B, the presence of a connector 13 with tabs 16 forces to maintain a phase, thus making it necessary to insert first the connector and only later the glenosphere 12A, thus introducing an additional step.

In other words, the first embodiment has the advantage of being able to assemble the connector 13 to the glenosphere 12A in advance and later to implant the assembly while allowing a position adjustment.

This aspect is often taken into consideration by surgeons to allow for an ease of adjustment and implantation.

Figure 13:
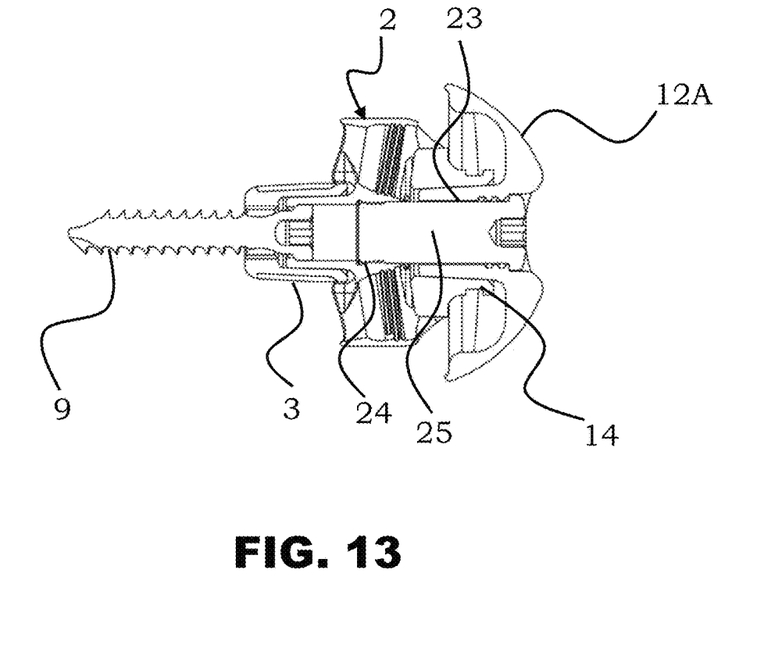
FIG. 13 shows a sectional view of the shoulder prosthesis according to the invention with a safety screw.

Moreover, the prosthesis 1 comprises a safety screw 25 adapted to keep all the elements of the prosthesis 1 itself in mutual coupling except for the pin 3 with its possible conical coupling (if not single-piece), as can be seen in the sectional view in FIG. 13. On the pin 3 it ensures however a further consolidation of the connection.

The safety screw 25 is inserted into a central hole 23 passing through the glenosphere 12A and actually coaxial with the hole 11 of the baseplate. The screw comprises a stem with a threaded end 24 that engages in a threaded manner with the internal thread 18 of the opening 11A of the hole 11 of the baseplate, thus keeping the mutual packing of all the components of the prosthesis 1, except for the pin 3.

Although there are obvious anatomical affinities between the patients who require the adoption of the prosthesis 1, it is well known that there are also some natural anatomical differences that must be taken into consideration for performing an optimal shoulder prosthesis implantation. From patient to patient it can be necessary to change the rotation centre of the glenosphere to correctly tension the soft tissues or to reposition it in a more advantageous position to favour appropriate biomechanics of the prosthesis (es. in medialized glenoids)

In this context, it is preferable to have the possibility to position the prosthesis 1, and in particular the glenosphere element 12, in a differentiated manner in different patients.

In greater detail, the prosthesis 1 according to the present disclosure allows the glenosphere 12A to be axially positioned, i.e. lateralized, with respect to the metaglene element 2, also ensuring different axial offsets. It is thereby possible to implant the prosthesis always having the tissues suitably tensioned.

Figure 14A:
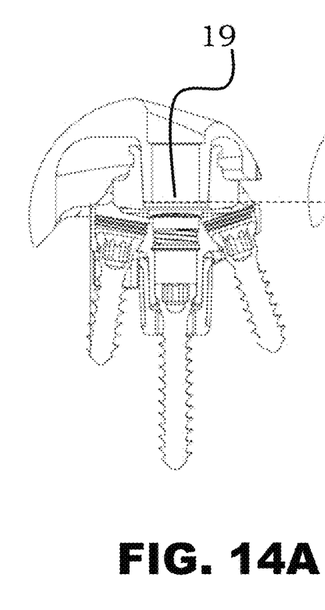
FIGS. 14A, 14B, 14C, show three connector elements with a different connecting portion according to the invention.

This possibility is offered by the device illustrated in FIGS. 14A to 14C that provides a variation in the configuration of the connector element 13 and, more particularly, in the portion 19 of this element intended for the coupling with the glenosphere.

To achieve this, the connecting portion 19 of the connector element 13 is varied in height, keeping the other features thereof unchanged.

In other words, identical connector elements 13 are adopted except for an axial dimension of this connecting portion 19, that varies in height being it adapted to generate an axial offset of the rotation centre of the glenosphere 12A preferably between 1 and 10 mm. By way of example, connector elements 13 with an axial dimension that varies between 3 mm and 6 mm are represented in FIGS. 14A, 14B, 14C.

In an alternative embodiment illustrated in FIG. 15, the prosthesis according to the present disclosure can be configured as an anatomical prosthesis 1' by means of a same interconnection and fixation solution between the component parts.

In the anatomical prosthesis 1' of FIG. 15, there is a metaglene element 2' or baseplate that is always intended to be inserted into a glenoid bone cavity but is coupled to a liner insert 12B.

The liner insert 12B is shaped to adapt to the metaglene element 2' of the anatomical prosthesis 1', that is structurally different from that of the previous exemplary embodiment.

This liner insert 12B has a projecting portion formed by a pair of elastic tines 20 that engage into a central hole 11' of the baseplate 2 in which a central compression screw 9 can be housed. The tines 20 provide small protuberances 21 that are elastically inserted at an annular cavity 22 obtained at the opening of the hole 11' so as to ensure the coupling of the liner insert 12B in the metaglene element 2'.

The liner insert 12B closes the metaglene element 2 at the top and is adapted to distribute at best the pressures at stake on the whole contact surface with the prosthesis 1'.

It is possible that the prosthesis 1' is implanted in an anatomical configuration and later, at a certain point of the patient's life, there is a degradation of the rotator cuff that suggests converting it into a reverse prosthesis 1, like that of the previous exemplary embodiment.

In other words, as can be seen in FIGS. 16A and 16B, the prostheses 1 and 1' are configured to be convertible, thus being it possible to convert the anatomical prosthesis 1' into a reverse prosthesis 1.

In particular, it is possible to remove the liner insert 12B and to add to the baseplate 2' the connector element 13 that allows the glenosphere element 12 to be associated by means of the safety screw 25.

Advantageously, the present invention allows the fixation between the prosthesis 1, 1' and the bone to be improved, with subsequent improvement in bone growth.

Consequently, the dimensions of the metaglene element 2 and also of the pin 3 can be reduced. With beneficial effects in the implantation and rehabilitation step.

Advantageously, specifically, the configuration of the present invention with the connector element having its housing seat, with respect to the prior art, allows an extra pin not to be adopted, thus allowing the metaglene diameter to be reduced by compressing everything towards the centre of the prosthesis.

Still advantageously, the present invention is particularly practical for surgeons who find themselves able to manipulate component parts that easily interconnect and without requiring a great vision effort during the complex surgical operating steps in areas that are difficult to access.

Finally, advantageously, the present invention can be modified and adjusted depending on the patients' specific needs.

The person skilled in the art will understand that the presented embodiment can be subjected to further modifications and variations, according to specific and contingent needs, all falling within the scope of protection of the invention, as defined by the following claims.

For example, the features described with regard to the reverse prosthesis that do not find technical impediments in an anatomical prosthesis can be translated without departing from the claimed scope of protection.

What is claimed is:

1. A shoulder prosthesis comprising:
   a metaglene element or baseplate;
   a pin projecting from said metaglene element or baseplate;
   a central through-hole in a centre of said metaglene element or baseplate;
   at least one through-hole formed in a periphery of the metaglene element or baseplate with respect to said central through-hole;
   a glenosphere element opposite said pin with respect to said metaglene element or baseplate;
   wherein the shoulder prothesis further comprises:
   a central compression screw housed in said central through-hole in the centre of said metaglene element or baseplate and having a head abutting onto a bottom of said central through-hole, said central through-hole having an opening that is threaded in a stretch to receive and threadably engage with a threaded end of a safety screw passing through the glenosphere element;
   a connector element between the metaglene element or baseplate and the glenosphere element, said metaglene element or baseplate providing a seat for housing said connector element, said seat projecting around said central through-hole.

2. The shoulder prosthesis according to claim 1, wherein said connector element is incorporated between the glenosphere and the metaglene or baseplate, and wherein a housing seat is formed as a single piece projecting around said central through-hole.

3. The shoulder prosthesis according to claim 1, wherein said connector element comprises a cone portion and said connecting seat is shaped with some crenelated portions angularly spaced apart from each other, said crenelated portions crown-projecting from the surface of the metaglene element or baseplate facing the side of the glenosphere.

4. The shoulder prosthesis according to claim 1, wherein a portion of said connector element has a positive engagement with said glenosphere element that is consolidated by the insertion of said safety screw.

5. The shoulder prosthesis according to claim 1, wherein said connector element can be coupled to said glenosphere element by a connecting portion with an axial dimension adapted to generate an axial displacement of a rotation centre of the glenosphere, said axial displacement comprised between 1 mm and 10 mm.

6. The shoulder prosthesis according to claim 1, wherein said pin is removable and constrained to a projection of said metaglene element or baseplate.

7. The shoulder prosthesis according to claim 1, wherein multiple through-holes having respective axes that are slanted with respect to a central axis of said metaglene element or baseplate are provided perimetrically to said central through-hole to house perimetrical fixing screws.

8. The shoulder prosthesis according to claim 1, wherein said safety screw is inserted through the glenosphere element having a threaded end engaging into the threaded opening of said central through-hole in the centre of said metaglene element or baseplate.

9. The shoulder prosthesis according to claim 1, wherein said metaglene element or baseplate and said pin are made in a single piece.

10. The shoulder prosthesis according to claim 1, wherein a locking element forming a closure after the insertion of said fixing screw is associated with an opening of said through-hole formed peripherally.

11. The shoulder prosthesis according to claim 10, wherein said locking element provides a hemispherical protuberance and the head of said fixing screw provides a frustoconical seat for housing said hemispherical protuberance.

12. The shoulder prosthesis according to claim 1, wherein said metaglene element or baseplate has an essentially cylindrical body and a diameter that is less or equal to 25 mm.

13. The shoulder prosthesis according to claim 1, wherein said metaglene element or baseplate comprises a trabecular structure or a surface coating layer on a surface configured to be in contact with a bone.

14. The shoulder prosthesis according to claim 1, said shoulder prosthesis being configured to be convertible, the central through-hole being further adapted to house a liner insert according to an anatomical configuration.

* * * * *